(12) United States Patent
Chien et al.

(10) Patent No.: US 10,426,874 B2
(45) Date of Patent: Oct. 1, 2019

(54) WOUND MANAGEMENT ASSEMBLY AND NEGATIVE PRESSURE WOUND THERAPY SYSTEM

(71) Applicant: APEX MEDICAL CORP., New Taipei (TW)

(72) Inventors: Chih-Tsan Chien, New Taipei (TW); Chiu-Yu Yeh, New Taipei (TW); Yeong-Sheng Chang, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 356 days.

(21) Appl. No.: 15/367,831

(22) Filed: Dec. 2, 2016

(65) Prior Publication Data

US 2018/0154052 A1 Jun. 7, 2018

(51) Int. Cl.

| | |
|---|---|
| *A61M 1/00* | (2006.01) |
| *A61F 13/00* | (2006.01) |
| *A61M 27/00* | (2006.01) |
| *A61M 13/00* | (2006.01) |
| *A61B 17/50* | (2006.01) |

(52) U.S. Cl.
CPC ...... *A61M 1/0088* (2013.01); *A61F 13/00068* (2013.01); *A61M 1/0019* (2013.01); *A61M 1/0027* (2014.02); *A61M 1/0056* (2013.01)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| | | | |
|---|---|---|---|
| 8,158,844 B2 | 4/2012 | McNeil | |
| 8,690,845 B2 * | 4/2014 | Long | A61M 1/0088 604/319 |
| 2011/0282309 A1 * | 11/2011 | Adie | A61M 1/0088 604/319 |

* cited by examiner

Primary Examiner — Tatyana Zalukaeva
Assistant Examiner — Ilya Y Treyger
(74) Attorney, Agent, or Firm — Muncy, Geissler, Olds & Lowe, P.C.

(57) ABSTRACT

The present disclosure relates to a wound management assembly. The wound management assembly comprises a housing and an exudate collector received in the housing. A gap is defined between the housing and the exudate collector to form a channel for fluid passage, wherein the fluid passes into and through the exudate collector and radially enters the channel.

21 Claims, 11 Drawing Sheets

WOUND MANAGEMENT ASSEMBLY AND NEGATIVE PRESSURE WOUND THERAPY SYSTEM

FIELD OF THE INVENTION

The present disclosure relates to medical therapy instruments for wound healing and, more particularly, to wound management assembly and negative pressure wound therapy system for channeling fluid from a wound.

BACKGROUND OF THE INVENTION

A wound caused by an injury typically produces blood, pus and material particles on and around the wound. If the wound is not compressed, bleeding may continue, and if the wound is not cleaned, the wound may become infected resulting in poor healing and further complications in recovery. A more serious wound typically produces a necrosis of coagulated blood, skin, and tissue. Over time, a scab of typically formed. Cleaning of the wound then would require the removal of material particles from the necrosis or scab. Particularly, for relatively large area wounds, the cleaning process may be difficult.

Negative pressure wound therapy system is extensively used for removing exudates from the wound and accelerating formulation of tissue. Typically, negative pressure is applied to the wound by a porous dressing. The porous dressing is often separated from the suction device to dispose into the wound site, and then the porous dressing is covered by the suction device. The disposal of the negative pressure wound therapy system may be more complicated. Furthermore, during operation, pus and particles with fluid may be deposited on surfaces within a tube of the suction device to obstruct the tube inhibiting the application of negative pressure to the wound, thereby defeating the effectiveness of therapy.

SUMMARY OF THE INVENTION

An objective of this disclosure is to provide a wound management assembly for promoting removal of fluid from a wound.

To achieve the aforesaid objective, the wound management assembly comprises a housing and an exudate collector received in the housing. A gap is defined between the housing and the exudate collector to form a channel for fluid passage, wherein the fluid passes into and through the exudate collector and radially enters the channel.

In one embodiment, the housing defines a chamber therein for receiving the exudate collector and comprises an inlet portion, an outlet and a side wall, the inlet portion and the outlet are in communication with the chamber, and the side wall encompasses the exudate collector.

In one embodiment, the housing further comprises at least one positioning element disposed in the chamber for positioning the exudate collector.

In one embodiment, the wound management assembly further comprises a sealing layer formed around the inlet portion.

In one embodiment, the sealing layer fittingly covers the wound.

In one embodiment, the sealing layer has a periphery provided with at least one rib.

In one embodiment, the inlet portion comprises a curved structure protruded toward the exudate collector and defining an inlet for the fluid passing into the exudate collector.

In one embodiment, the exudate collector has a plurality of fluid paths with different lengths from the inlet to the channel.

In one embodiment, the housing comprises a drop-shaped structure having a blunt end connected with the sealing layer and a tip end spaced apart from the sealing layer.

In one embodiment, the housing and the sealing layer are integrally formed as a one-piece structure.

In one embodiment, the exudate collector is substantially orthogonal to the side wall.

In one embodiment, the exudate collector is surrounded by the channel.

In one embodiment, the channel is separated from two symmetrical passages by the exudate collector and the two symmetrical passages are converged to a single passage on the outlet.

In one embodiment, in a reduced pressure state, the fluid is removed from the wound in a direction substantially perpendicular to the wound and radially directed to the channel in a direction parallel to the exudate collector.

In one embodiment, in the reduced pressure state, the fluid flows in the channel at a rate faster than the fluid flows in the exudate collector.

In one embodiment, the exudate collector is constructed from a porous material.

In one embodiment, the exudate collector is constructed from at least one predetermined fabric layer.

In one embodiment, the exudate collector is constructed from a plurality of predetermined fabric layers which are comprised of different pore sizes.

In one embodiment, the exudate collector is constructed from at least one hydrophilic material and at least one hydrophobic material.

In one embodiment, a pressure sensitive element is disposed on the exudate collector whereby the pressure sensitive element changes color by the housing touching the pressure sensitive element in a reduced pressure state.

In one embodiment, a window is disposed on the housing, through which the exudate collector is aligned with the chamber.

In one embodiment, a hole is disposed on the exudate collector aligned with the window, through which the condition of the wound is observed.

Also disclosed herein is a negative pressure wound therapy system. The negative pressure wound therapy system comprises a negative pressure source, a tube, and a wound management assembly. The wound management assembly comprises a housing and an exudate collector received in the housing. A gap is defined between the housing and the exudate collector to form a channel for fluid passage, wherein the fluid passes into and through the exudate collector and radially enters the channel.

BRIEF DESCRIPTION OF THE DRAWINGS

A more complete understanding of the subject matter can be derived by referring to the detailed description and claims when considered in conjunction with the following figures, wherein like reference numbers refer to similar elements throughout the figures.

DETAILED DESCRIPTION OF THE INVENTION

Since various aspects and embodiments are merely exemplary and not limiting, after reading this specification, skilled artisans appreciate that other aspects and embodiments are possible without departing from the scope of the invention. Other features and benefits of any one or more of the embodiments will be apparent from the following detailed description and the claims.

The use of "a" or "an" is employed to describe elements and components described herein. This is done merely for convenience and to give a general sense of the scope of the invention. Accordingly, this description should be read to include one or at least one and the singular also includes the plural unless it is obvious that it is meant otherwise.

Furthermore, as used herein, the terms "comprises," "comprising," "includes," "including," "has," "having" or any other variation thereof are intended to cover a non-exclusive inclusion. For example, a component, structure, article, or apparatus that comprises a list of elements is not necessarily limited to only those elements but may include other elements not expressly listed or inherent to such component, structure, article, or apparatus.

As used herein, an exudate is a fluid emitted from a wound of the body. The exudate collector of the present disclosure is utilized to compress the wound and absorb fluid from the wound and at the same time through suction, channel the fluid and filter out any material particles, thereby ensuring a thorough cleaning of the wound.

Figure 1:
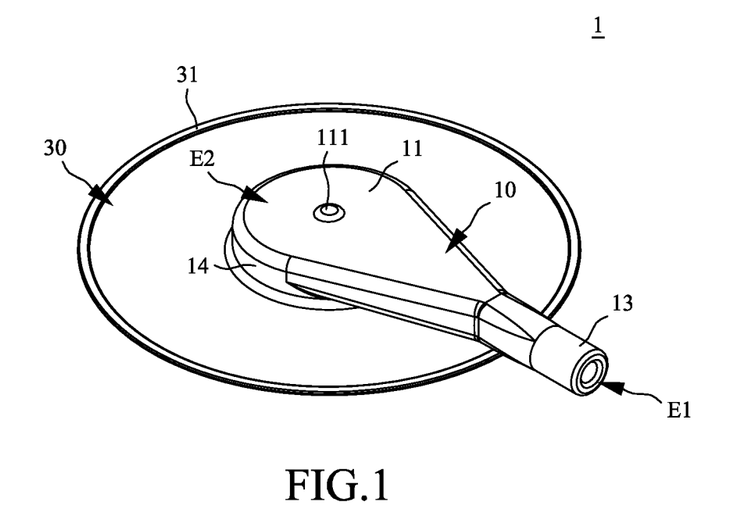
FIG. 1 illustrates a view of the first embodiment of a wound management assembly according to the present disclosure.
Figure 2:
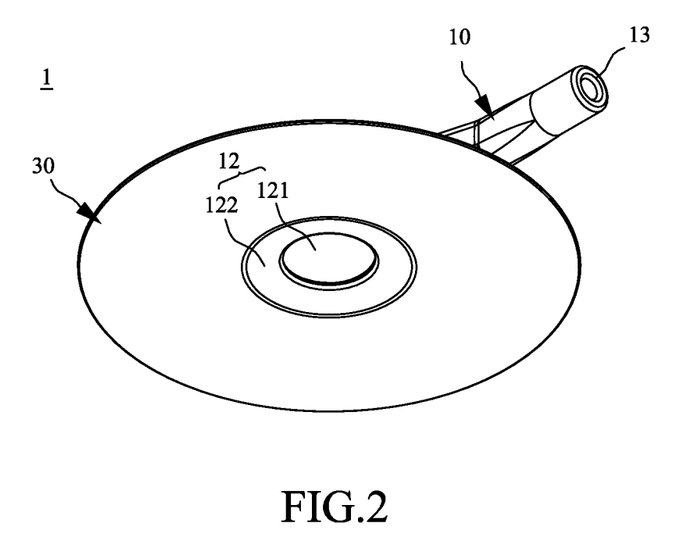
FIG. 2 illustrates another view of the first embodiment of the wound management assembly according to the present disclosure.
Figure 3:
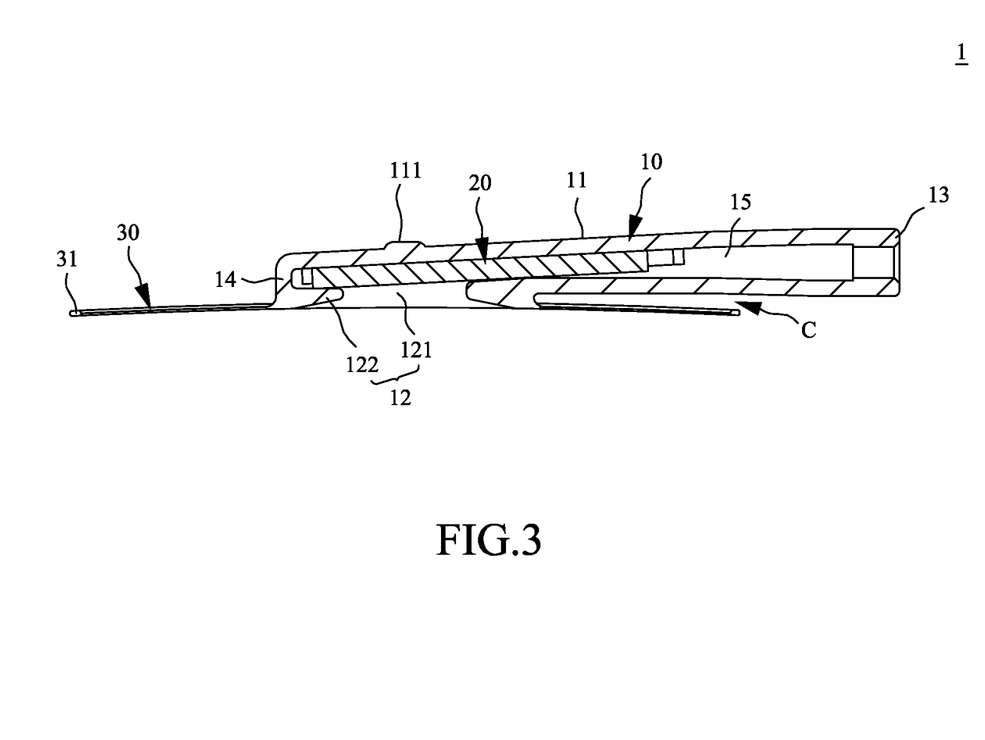
FIG. 3 illustrates a cross-sectional view of the first embodiment of the wound management assembly according to the present disclosure.

Refer concurrently to FIG. 1 to FIG. 3, wherein FIG. 1 illustrates a view of the first embodiment of the wound management assembly 1, FIG. 2 illustrates another view of the first embodiment of the wound management assembly 1, and FIG. 3 illustrates a cross-sectional view of the first embodiment of the wound management assembly 1. As shown in FIG. 1 to FIG. 3, in the first embodiment of the present disclosure, the wound management assembly 1 comprises a housing 10 and an exudate collector 20, and the exudate collector 20 is received in the housing 10. The housing 10 defines a chamber 15 therein for receiving the exudate collector 20, and the housing 10 comprises a top portion 11, an inlet portion 12, an outlet 13 and a side wall 14. The top portion 11 is disposed corresponding to the inlet portion 12, and two sides of the side wall 14 are connected to the top portion 11 and the inlet portion 12 respectively. The inlet portion 12 and the outlet 13 are in fluid communication with the chamber 15, so that fluid from the wound may flow into the chamber 15 through the inlet portion 12 and then flow out into the outlet 13.

In one embodiment of the present disclosure, the wound management assembly 1 further comprises a sealing layer 30. The sealing layer 30 is connected to the housing 10 and is formed around the inlet portion 12. The sealing layer 30 is used for contacting the skin around the wound to form a sealing environment. An adhesive material may be formed on the surface of the sealing layer 30 facing the wound for attaching to the skin around the wound.

The sealing layer 30 fittingly covers the wound. It means that the sealing layer 30 and the skin around the wound are fit close together. For example, the sealing layer 30 may be constructed from a flexible and deformable material adapted for covering the wound on any part of a human body, such as using a silicone material, but this disclosure is not limited thereto. Furthermore, the sealing layer 30 may be designed for different shapes, such as a circle, a rectangle, a star-shape, a serration or other shapes. In one embodiment of the present disclosure, the sealing layer 30 is a circle, and the thickness of the sealing layer 30 is less than or equal to 0.8 mm.

In one embodiment of the present disclosure, the sealing layer 30 has a periphery provided with at least one rib 31. The rib 31 is used for enhancing the tensile strength of the sealing layer 30, so that it is avoided breaking or damaging the sealing layer 30 during producing or usage of the sealing layer 30. In this embodiment, the rib 31 forms an annular structure, and the thickness of the rib 31 is more than 0.8 mm.

The inlet portion 12 comprises a curved structure 122 protruded toward the exudate collector 20 and defining an inlet 121 for the fluid passing into the exudate collector 20. In this embodiment, the inlet 121 is disposed at the central of the curved structure 122. Therefore, when the wound management assembly 1 is placed on the wound and forms a reduced pressure environment, the function of reduced pressure may be increased by the disposal of the curved structure 122.

As shown in FIG. 1 to FIG. 3, in one embodiment of the present disclosure, a positional portion 111 is disposed on the top portion 11, and the position of the positional portion 111 is corresponding to the inlet 121 of the inlet portion 12. When the wound management assembly 1 would be placed on the wound, the inlet 121 of the inlet portion 12 is aligned with the wound by the positional portion 111.

In the preferred embodiment of the present disclosure, the housing 10 is a drop-shaped structure, and the drop-shaped structure has a tip end E1 and a blunt end E2. The blunt end E2 is connected with the sealing layer 30, and the tip end E1 is spaced apart from the sealing layer 30. Particularly, an interval C is formed between the tip end E1 and the sealing layer 30, so that the movement of the tip end E1 would not influence the contact between the sealing layer 30 and the skin by the interval C when the wound management assembly 1 is placed on the wound.

In one embodiment of the present disclosure, the housing 10 and the sealing layer 30 are integrated formed as a one-piece structure, but this disclosure is not limited thereto.

Figure 4:
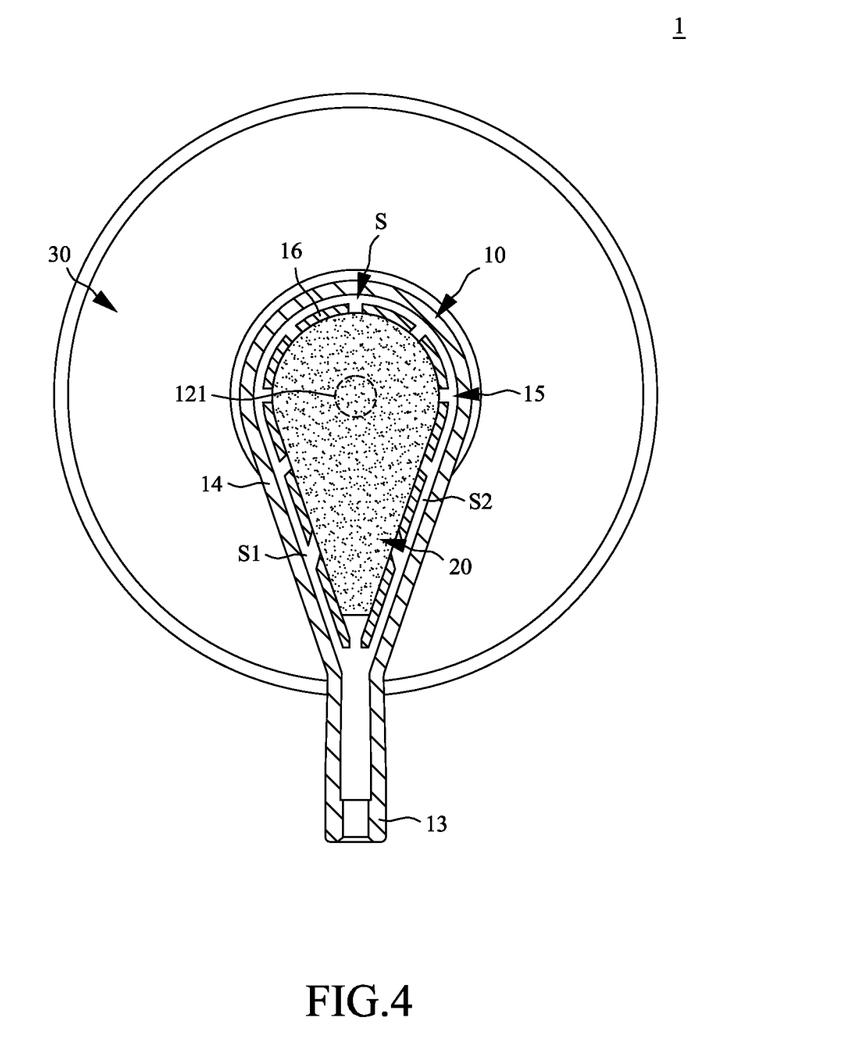
FIG. 4 illustrates another cross-sectional view of the first embodiment of the wound management assembly according to the present disclosure.

Refer concurrently to FIG. 3 and FIG. 4, wherein FIG. 4 illustrates another cross-sectional view of the first embodiment of the wound management assembly 1. As shown in FIG. 3 and FIG. 4, the exudate collector 20 is disposed within the chamber 15 of the housing 10. Two opposite faces of the exudate collector 20 are contacted respectively to the top portion 11 and the inlet portion 12, and the side wall 14 substantially encompasses the exudate collector 20. The exudate collector 20 is used for collecting the fluid from the wound, filtering pus of the fluid, and channeling the fluid to change flow directions. Furthermore, in one embodiment of the present disclosure, each of the two opposite faces of the exudate collector 20 is substantially orthogonal to the side wall 14, so that the fluid flowed perpendicularly into the exudate collector 20 from the inlet portion 12 may be channeled to flow horizontally out of the exudate collector 20 for changing flow directions.

A gap is defined between the housing 10 and the exudate collector 20 to form a channel S for fluid passage. In the preferred embodiment of the present disclosure, the gap is formed between the exudate collector 20 and the side wall 14 as the channel S, and the exudate collector 20 is surrounded by the channel S. For example, the width of gap is greater than or equal to 1.0 mm. Furthermore, for positioning the location of the exudate collector 20 and the width of gap, in one embodiment of the present disclosure, the housing 10 further comprises at least one positioning element 16 disposed in the chamber 15. The at least one positioning element 16 may be disposed on the surface of the top portion 11 facing the chamber 15 for positioning the exudate collector 20, and the channel S is between the at least one positioning element 16 and the side wall 14.

In one embodiment of the present disclosure, the exudate collector 20 may be constructed from a porous material. The porous material may be open-cell foam, such as polyurethane foam, but this disclosure is not limited thereto. The porous material has a plurality of irregular pores distributed through the structure of the porous material so as to provide a plurality of fluid paths with different flow directions and a filtering function for the fluid. In one embodiment, the size of each pore is about 300~1200 μm. Furthermore, in this embodiment, the exudate collector 20 is also a drop-shaped structure corresponding to the shape of the housing 10.

Figure 5:
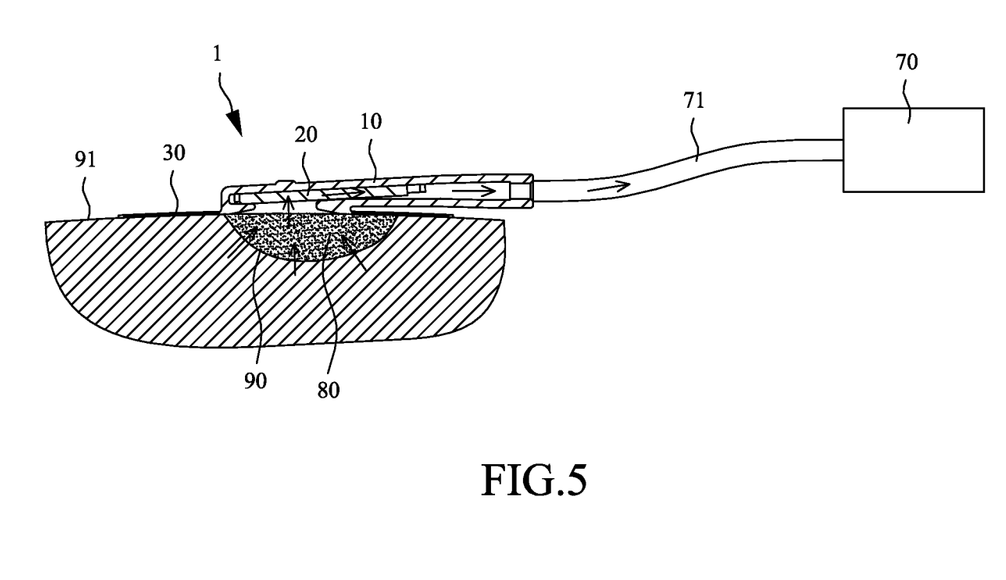
FIG. 5 illustrates a view of fluid flowing status of the first embodiment of the wound management assembly according to the present disclosure.
Figure 6:
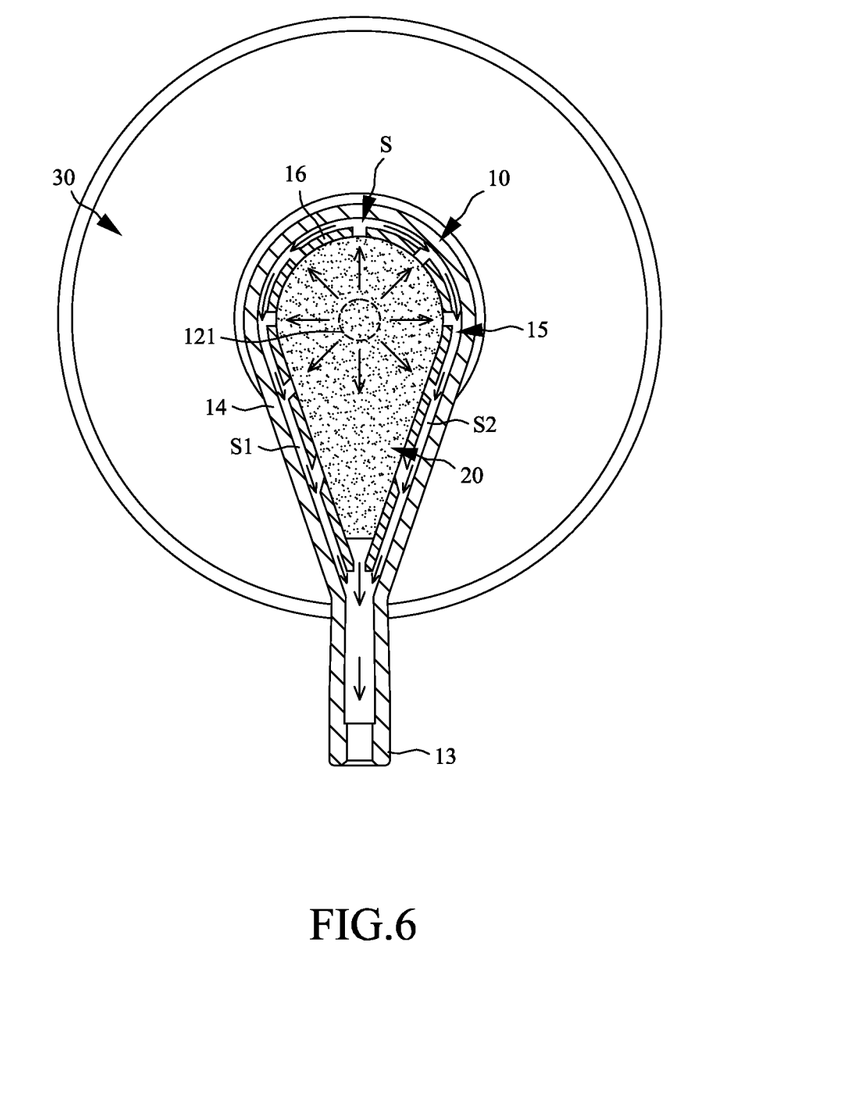
FIG. 6 illustrates another view of fluid flowing status of the first embodiment of the wound management assembly according to the present disclosure.

Refer concurrently to FIG. 5 and FIG. 6, wherein FIG. 5 illustrates a view of fluid flowing status of the first embodiment of the wound management assembly 1, and FIG. 6 illustrates another view of fluid flowing status of the first embodiment of the wound management assembly 1. As shown in FIG. 5, the wound management assembly 1 is connected to a negative pressure source 70 by a tube 71. A wound dressing 80 is disposed on the wound 90, and the housing 10 is placed corresponding to the wound 90 and contacted with the skin 91 around the wound 90 by the sealing layer 30 for sealing the wound 90.

In operation, the negative pressure source 70 is executed for reducing pressure to the wound 90 by the tube 71, so that the reduced pressure environment is formed between the wound 90 and the negative pressure source 70. In a reduced pressure state, the fluid (such as exudate, blood, or pus) is removed from the wound 70 in a direction substantially perpendicular to the wound 70 to the wound management assembly 1. The fluid is absorbed by the wound dressing 80 first and then is sucked into the chamber 15 of the housing 10 through from the inlet 121 of inlet portion 12. As shown in FIG. 5 and FIG. 6, the fluid flowed into the chamber 15 passes into and through the exudate collector 20 and then flows radially to enter the fluid channel S surrounded the exudate collector 20, so as to change flow directions of the fluid. Particularly, the fluid is radially directed to the channel S in a direction parallel to the exudate collector 20.

Furthermore, in this embodiment, the exudate collector 20 is also a drop-shaped structure corresponding to the shape of the housing 10, and distances from the inlet 121 to a periphery of the exudate collector 20 are different. Therefore, the exudate collector 20 has a plurality of fluid paths with different lengths from the inlet 121 to the channel S. Accordingly, the fluid may pass into and through the exudate collector 20 for a time, and the fluid may be collected and filtered by the exudate collector 20. Some material particles or pus in the fluid may be filtered and kept in the exudate collector 20.

Finally, the fluid entered the channel S may be directed along the channel S to the outlet 13. As shown in FIG. 6, in this embodiment, the channel S is separated from two symmetrical passages S1, S2 by the exudate collector 20, and the two symmetrical passages S1, S2 are converged to a single passage on the outlet 13. The surrounding channel S effectively directs the filtered fluid around all areas of the exudate collector 20, and the filtered fluid efficiently converges on the outlet 13 to flow into the tube 71.

On the other hand, the width of gap (channel S) is far more than the size of the pore in the exudate collector 20. In the reduced pressure state, the fluid flows in the channel S at a rate faster than the fluid flows in the exudate collector 20. Accordingly, the fluid may be directed effectively by the disposal of the channel S.

Furthermore, as shown in FIG. 5, in the preferred embodiment of the present disclosure, for some wounds, the wound dressing 80 may be removed and replaced completely by the exudate collector 20 within the chamber 15 in functions. It means that the fluid removed from the wound 70 may be directly absorbed by the exudate collector 20 through the inlet 121 of inlet portion 12 without the wound dressing 80. Accordingly, the exudate collector 20 may provide various functions for collecting the fluid, filtering the fluid, and channeling the fluid.

Figure 7A:
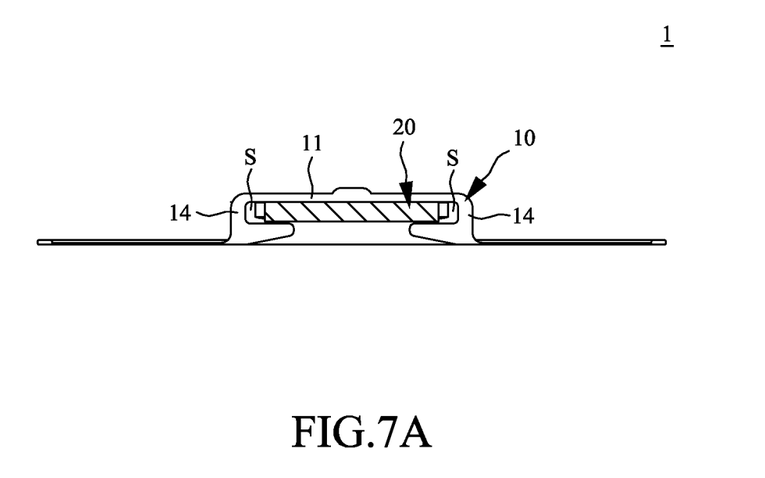
FIG. 7A illustrates a partial cross-sectional view of the first embodiment of the wound management assembly according to the present disclosure before reducing pressure.
Figure 7B:
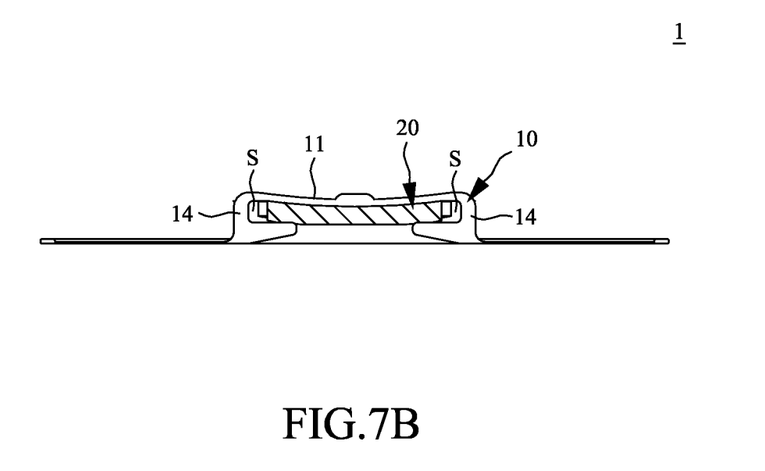
FIG. 7B illustrates a partial cross-sectional view of the first embodiment of the wound management assembly according to the present disclosure after reducing pressure.

Refer concurrently to FIG. 7A and FIG. 7B, wherein FIG. 7A illustrates a partial cross-sectional view of the first embodiment of the wound management assembly 1 before reducing pressure, and FIG. 7B illustrates a partial cross-sectional view of the first embodiment of the wound management assembly 1 after reducing pressure. As shown in FIG. 7A, in one embodiment of the present disclosure, the side wall 14 has a thickness greater than that of the top portion 11. When pressure is reduced by the negative pressure source, as shown in FIG. 7B, the top portion 11 would be caved in toward the exudate collector 20, and at the same time, the side wall 14 may provide enough support force for supporting the top portion 11 and keep the fluid channel S unobstructed. Furthermore, the enhancement of the structure of the side wall 14 would improve the effectiveness of the pressure feedback.

Figure 8A:
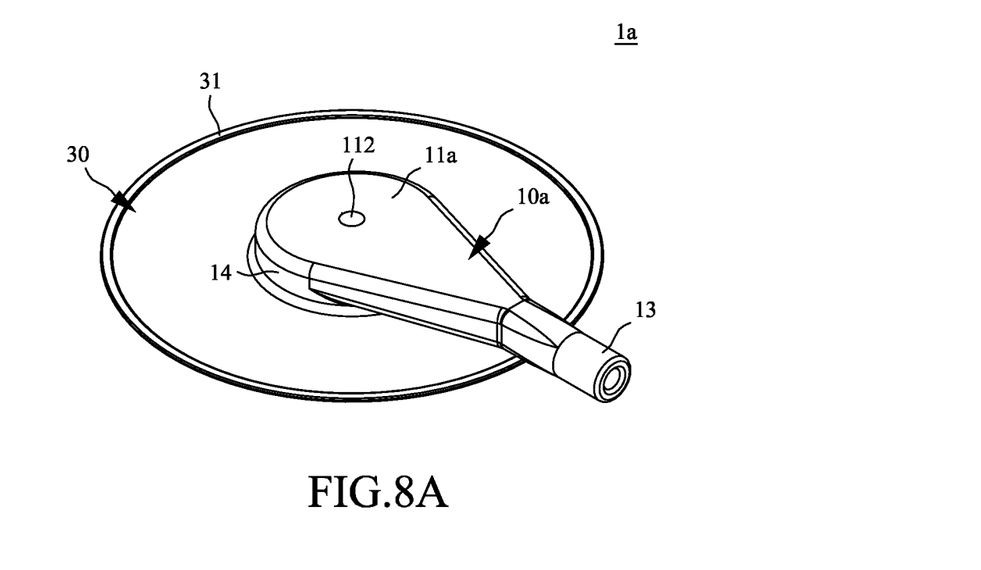
FIG. 8A illustrates a view of the second embodiment of the wound management assembly.
Figure 8B:
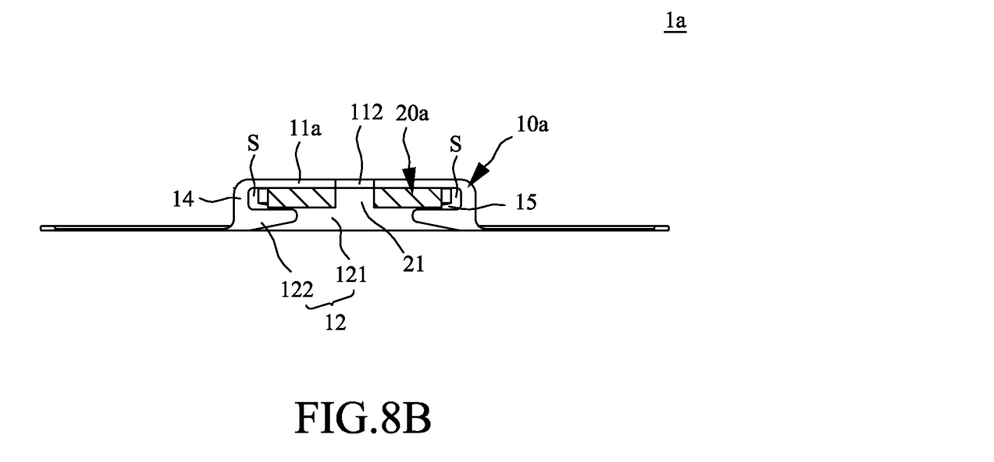
FIG. 8B illustrates a partial cross-sectional view of the second embodiment of the wound management assembly after reducing pressure.

Refer concurrently to FIG. 8A and FIG. 8B, wherein FIG. 8A illustrates a view of the second embodiment of the wound management assembly 1a, and FIG. 8B illustrates a partial cross-sectional view of the second embodiment of the wound management assembly 1a after reducing pressure. As shown in FIG. 8A and FIG. 8B, in the preferred embodiment of the present disclosure, a window 112 is disposed on the top portion 11a, through which the exudate collector 20a is aligned with the chamber 15 is observed. In addition, a hole 21 is disposed in the exudate collector 20a, and the position of the hole 21 is corresponding to the window 112 of the top portion 11a and the inlet 121 of the inlet portion 12. Accordingly, the condition of the wound is allowed to be observed through the window 112 of the housing 10a and the hole 21 the exudate collector 20a.

Figure 9A:
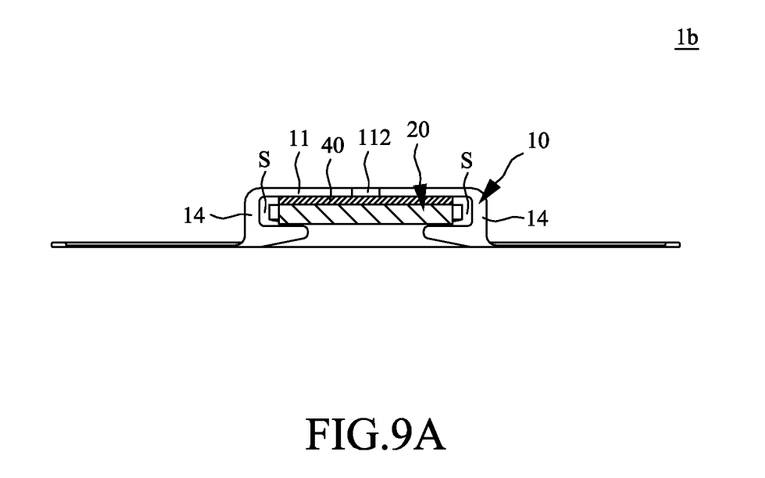
FIG. 9A illustrates a partial cross-sectional view of the third embodiment of the wound management assembly before reducing pressure.
Figure 9B:
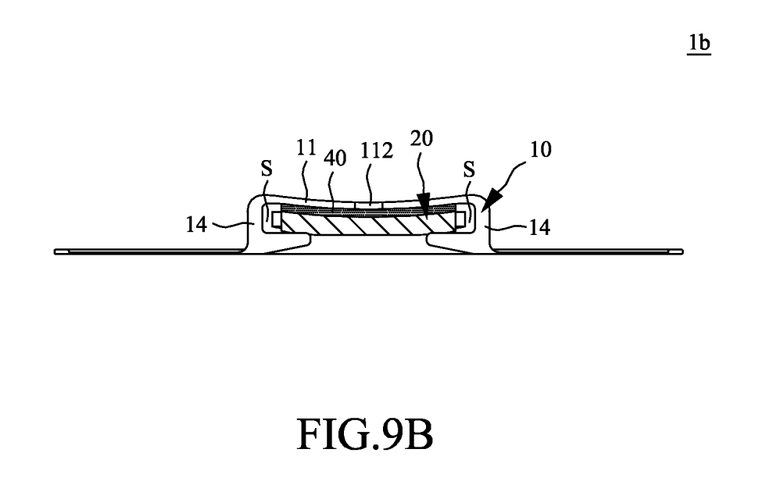
FIG. 9B illustrates a partial cross-sectional view of the third embodiment of the wound management assembly after reducing pressure.

Refer concurrently to FIG. 9A and FIG. 9B, wherein FIG. 9A illustrates a partial cross-sectional view of the third embodiment of the wound management assembly 1b before reducing pressure, and FIG. 9B illustrates a partial cross-sectional view of the third embodiment of the wound management assembly 1b after reducing pressure. As shown in FIG. 9A, in one embodiment of the present disclosure, a pressure sensitive element 40 with a piezochromism property, such as a piezochromic element or a pressure sensitive electrochromic element, is disposed on the exudate collector 20 and faced to the top portion 11 of the housing 10. As shown in FIG. 9B, in a reduced pressure state, the top portion 11 would be caved in toward the exudate collector 20 and touch the pressure sensitive element 40, so that the pressure sensitive element 40 may change color in response to pressure changes. Accordingly, the pressured condition of the exudate collector 20 is allowed to be observed from the windows 112 of the housing 10 by color changes of the pressure sensitive element 40 for monitoring the operation of the wound management assembly 1b.

In another embodiment of the present disclosure, the exudate collector may be constructed from at least one predetermined fabric layer. For example, the exudate collector may be a single predetermined fabric layer. The single predetermined fabric layer has a plurality of regular pores so as to provide a plurality of fluid paths and a filtering function. The exudate collector may also be a plurality of predetermined fabric layers which are comprised of different pore sizes. Therefore, the plurality of predetermined fabric layers also provide a plurality of fluid paths with different flow directions and a filtering function for the fluid.

Figure 10:
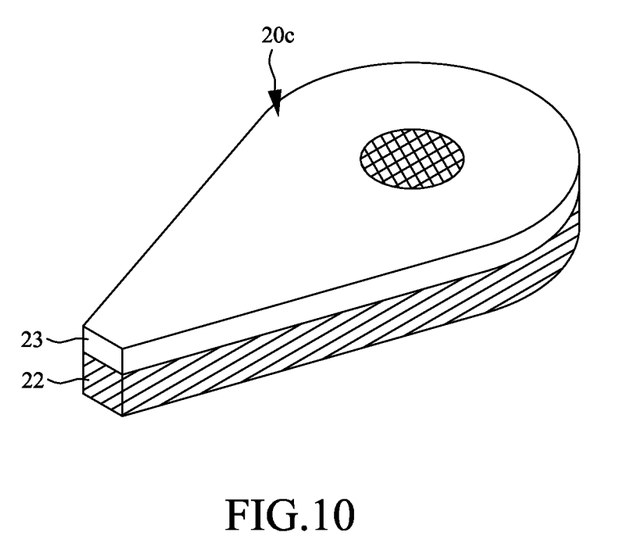
FIG. 10 illustrates a view of the exudate collector of the fourth embodiment of the wound management assembly.

Refer to FIG. 10 illustrates a view of the exudate collector 20c of the fourth embodiment of the wound management assembly. As shown in FIG. 10, in one embodiment of the present disclosure, the exudate collector 20c is constructed from at least one hydrophilic material 22 and at least one hydrophobic material 23. The exudate collector 20c is a laminar structure, and the hydrophilic material 22 has a thickness greater than that of the hydrophobic material 23. When the exudate collector 20c is disposed within the housing (not shown in FIG. 9, please see FIG. 3), the hydrophilic material 22 is contacted with the inlet portion 12 of the housing 10, and the hydrophobic material 23 is contacted with the top portion 11 of the housing 10. Accordingly, the fluid may be prevented to flow out from the contacting surface between the hydrophobic material 23 and the top portion 11 of the housing 10 by the hydrophobic material 23 and may flow along the hydrophilic material 22.

Figure 11A:
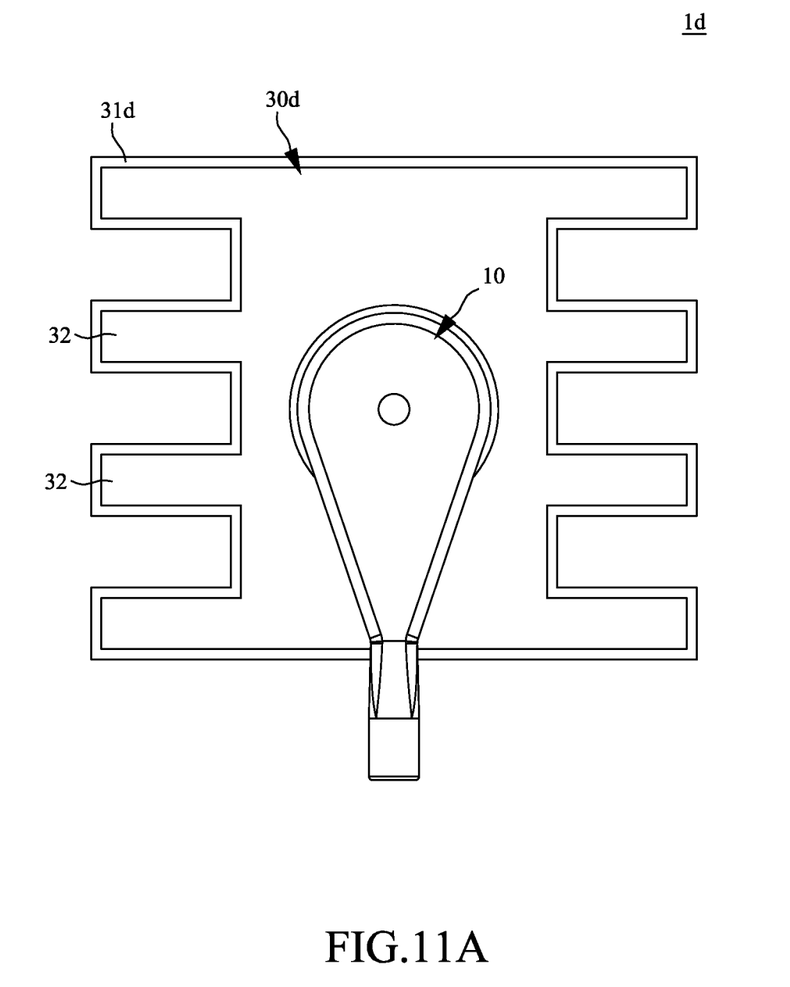
FIG. 11A illustrates a view of the fifth embodiment of the wound management assembly.
Figure 11B:
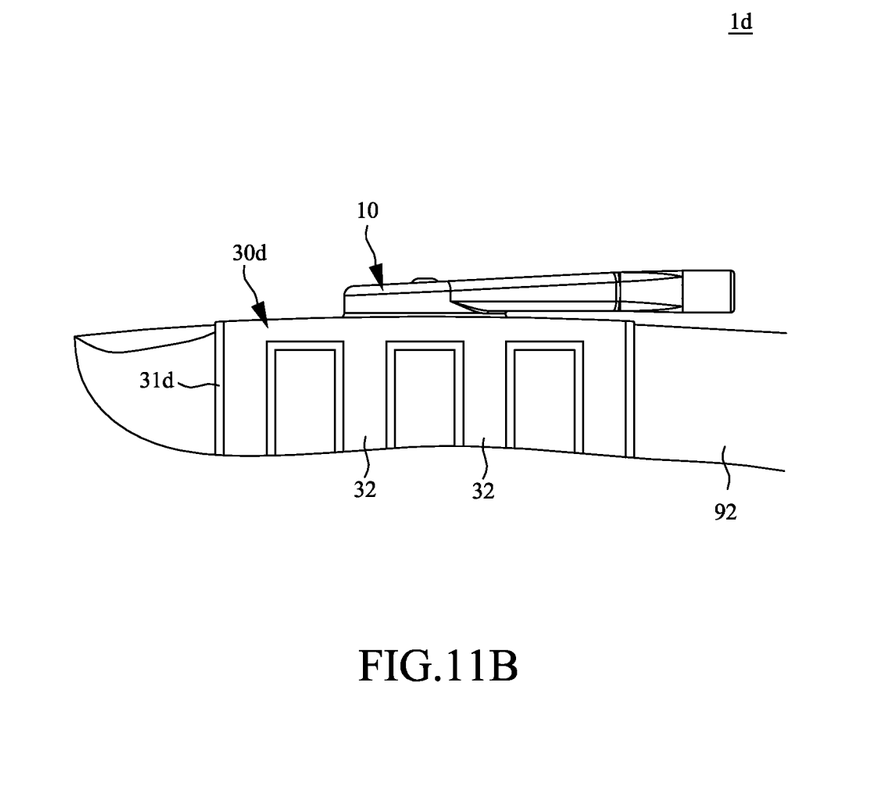
FIG. 11B illustrates a schematic diagram of using the fifth embodiment of the wound management assembly.

Refer concurrently to FIG. 11A and FIG. 11B, wherein FIG. 11A illustrates a view of the fifth embodiment of the wound management assembly 1d, and FIG. 11B illustrates a schematic diagram of using the fifth embodiment of the wound management assembly 1d. As shown in FIG. 11A, in one embodiment of the present disclosure, the sealing layer 30d of the wound management assembly 1d is designed for a rectangle element 33 with a plurality of strips 32. Each strip 32 is disposed individually and one side of each strip 32 is connected to the periphery of the rectangle element 33. One surface of the strip 32 facing the wound has an adhesive material. As shown in FIG. 11B, for example, when the wound is formed on a finger 92 or an ankle, the housing 10 of the wound management assembly 1d may be aligned with the wound. The sealing layer 30d covers the wound, and the sealing layer 30d is fixed on the finger 92 by winding the plurality of strips 32 around the finger 92. Therefore, the wound management assembly 1d may be used for providing better sealing and fixing function when the wound is formed on a special part of a human body without enough flat areas.

Please return to FIG. 5, the present disclosure further comprises a negative pressure wound therapy system. The negative pressure wound therapy system comprises the aforementioned wound management assembly 1, 1a, 1b, or 1d, a tube 71, and a negative pressure source 70. The wound management assembly 1, 1a, 1b or 1d is in fluid communication with the negative pressure source 70 through the tube 71, so that the negative pressure may be delivered to the wound 90 by the tube 71 and the wound management assembly 1, 1a, 1b or 1d.

Accordingly, the wound management assembly of the present disclosure integrates the exudate collection and filter material with the suction member to increase the availability and the convenience for disposal. The channel formed between the exudate collector and the side wall of the housing may channel the fluid efficiently.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any appropriate suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A wound management assembly for promoting removal of fluid from a wound, comprising:
   a housing comprising an inlet portion, an outlet and a side wall;
   an exudate collector received in the housing; and
   a gap defined between the housing and the exudate collector to form a channel for fluid passage;
   wherein the fluid passes into and through the exudate collector and radially enters the channel;
   wherein the housing defines a chamber therein for receiving the exudate collector, and the inlet portion and the outlet are in communication with the chamber; and
   wherein the side wall encompasses the exudate collector, and the exudate collector is surrounded by the channel.

2. The wound management assembly of claim 1, wherein the housing further comprises at least one positioning element disposed in the chamber for positioning the exudate collector.

3. The wound management assembly of claim 1, further comprising a sealing layer formed around the inlet portion.

4. The wound management assembly of claim 3, wherein the sealing layer fittingly covers the wound.

5. The wound management assembly of claim 3, wherein the sealing layer has a periphery provided with at least one rib.

6. The wound management assembly of claim 3, wherein the inlet portion comprises a curved structure protruded toward the exudate collector and defining an inlet for the fluid passing into the exudate collector.

7. The wound management assembly of claim 6, wherein the exudate collector has a plurality of fluid paths with different lengths from the inlet to the channel.

8. The wound management assembly of claim 3, wherein the housing comprises a drop-shaped structure having a blunt end connected with the sealing layer and a tip end spaced apart from the sealing layer.

9. The wound management assembly of claim 3, wherein the housing and the sealing layer are integrally formed as a one-piece structure.

10. The wound management assembly of claim 1, wherein the exudate collector is substantially orthogonal to the side wall.

11. The wound management assembly of claim 1, wherein the channel is separated from two symmetrical passages by the exudate collector and the two symmetrical passages are converged to a single passage on the outlet.

12. The wound management assembly of claim 1, wherein in a reduced pressure state, the fluid is removed from the wound in a direction substantially perpendicular to the wound and radially directed to the channel in a direction parallel to the exudate collector.

13. The wound management assembly of claim 12, wherein in the reduced pressure state, the fluid flows in the channel at a rate faster than the fluid flows in the exudate collector.

14. The wound management assembly of claim 1, wherein the exudate collector is constructed from a porous material.

15. The wound management assembly of claim 1, wherein the exudate collector is constructed from at least one predetermined fabric layer.

16. The wound management assembly of claim 15, wherein the exudate collector is constructed from a plurality of predetermined fabric layers which are comprised of different pore sizes.

17. The wound management assembly of claim 1, wherein the exudate collector is constructed from at least one hydrophilic material and at least one hydrophobic material.

18. The wound management assembly of claim 1, wherein a pressure sensitive element is disposed on the exudate collector whereby the pressure sensitive element changes color by the housing touching the pressure sensitive element in a reduced pressure state.

19. The wound management assembly of claim 1, wherein a window is disposed on the housing, through which the exudate collector is aligned with the chamber.

20. The wound management assembly of claim 19, wherein a hole is disposed on the exudate collector aligned with the window, through which the condition of the wound is observed.

21. A negative pressure wound therapy system comprising:
   a negative pressure source;
   a tube; and
   a wound management assembly, being connected to the negative pressure source through the tube, the wound management assembly comprising:
   a housing comprising an inlet portion, an outlet and a side wall;
   an exudate collector received in the housing; and
   a gap defined between the housing and the exudate collector to form a channel for fluid passage;
   wherein the fluid passes into and through the exudate collector and radially enters the channel;
   wherein the housing defines a chamber therein for receiving the exudate collector, and the inlet portion and the outlet are in communication with the chamber; and
   wherein the side wall encompasses the exudate collector, and the exudate collector is surrounded by the channel.

* * * * *